United States Patent [19]

Klotz

[11] Patent Number: 5,358,471
[45] Date of Patent: Oct. 25, 1994

[54] WRIST BRACE

[76] Inventor: John S. Klotz, 3417 S. 59th St., Belleville, Ill. 62223

[21] Appl. No.: 36,457

[22] Filed: Mar. 24, 1993

[51] Int. Cl.$^5$ .......................... A61F 5/04; A61F 5/10
[52] U.S. Cl. ...................................... 602/21; 602/20; 602/16; 602/5
[58] Field of Search .................... 602/20, 21, 16, 5, 64; 128/26; 623/21; 273/189 R, 189 A; 482/44

[56] References Cited

U.S. PATENT DOCUMENTS

| | | | |
|---|---|---|---|
| 4,149,532 | 4/1979 | Terry et al. | 128/77 |
| 4,237,873 | 12/1980 | Terry et al. | 128/77 |
| 4,259,949 | 4/1981 | Axelsson | 128/77 |
| 4,585,228 | 4/1986 | Olson | 272/119 |
| 4,660,550 | 4/1987 | Bodine | 128/77 |
| 4,679,548 | 7/1987 | Pecheux | 128/26 |
| 4,772,012 | 9/1988 | Chesher | 272/67 |
| 4,873,968 | 10/1989 | Finnieston et al. | 602/21 |
| 4,960,114 | 10/1990 | Dale | 128/87 R |
| 4,977,890 | 12/1990 | Mann | 128/77 |
| 5,002,044 | 3/1991 | Carter | 602/21 X |
| 5,176,623 | 1/1993 | Stetman et al. | 602/27 |

OTHER PUBLICATIONS

Color photocopies of photographs showing rigid hand brace made by Southern Illinois Prosthetic, was in public use prior to Mar. 24, 1992.

*Primary Examiner*—Stephen R. Crow
*Assistant Examiner*—Beverly A. Meindl
*Attorney, Agent, or Firm*—Senniger, Powers, Leavitt & Roedel

[57] ABSTRACT

A wrist brace for therapeutic support of a wrist of a patient comprising a forearm support member and a hand engageable member. The forearm support member has a base portion engageable with a forearm of the patient and first and second side portions extending from the base portion and adapted for traversing opposite sides of the wrist of the patient when the forearm is engaged by the forearm support member. The hand engageable member has a hand grip for supporting the palm or fingers of the patient and a hand grip support for spacing the hand grip from the forearm support member. The hand grip support comprises first and second side portions. The first side portion has a first grip securing region connected to a first end of the hand grip and a first wrist region. The second side portion has a second grip securing region connected to a second end of the hand grip and a second wrist region. At least one connector pivotally connects the first and second wrist regions to the first and second side portions of the forearm support member, respectively, for pivotal movement of the hand engageable member relative to the forearm support member from a wrist dorsiflexion position to a wrist palmarflexion position about a pivot axis generally coaxial with a wrist axis passing through the radioulnar joint of the wrist of the patient when the patient is wearing the wrist brace. The hand engageable member is lockable to the forearm support member by a locking mechanism in any one of a plurality of predetermined positions between the dorsiflexion position and the palmarflexion position.

12 Claims, 4 Drawing Sheets

WRIST BRACE

BACKGROUND OF THE INVENTION

This invention relates generally to therapeutic braces and, more particularly, to a wrist brace for therapeutic support of a wrist of a patient.

Frequently, after a stroke or after the onset of a muscle-attacking disease, such as cerebral palsy, a patient's hand may become involuntarily closed or clenched and the wrist may be involuntarily fixed in a palmarflexion position. So that the patient may have use of his or her hands, it is desirable that the patient undergo therapy to open the clenched fist and to urge the wrist toward a neutral or dorsiflexion position.

Splints and braces are typically used to hold the wrist in a neutral position. The angle at which the splints and braces hold the wrist is generally not adjustable with such splints and braces. However, the desirable degree of flexion or extension may vary from patient to patient and may even vary in an individual patient depending upon the progress of the patient's therapy. Thus, a single brace construction may not accommodate different patients and may not accommodate an individual patient throughout his or her entire therapy.

SUMMARY OF THE INVENTION

Among the objects of the present invention may be noted the provision of an improved wrist brace which overcomes the disadvantages and deficiencies associated with the prior art devices; the provision of such a wrist brace capable of acommodating various degrees of flexion or extension; the provision of such a wrist brace in which the degree of flexion or extension of the wrist may be varied; the provision of such a wrist brace in which the discomfort to a patient is minimized; and the provision of such a wrist brace which is of relatively simple construction.

Generally, a wrist brace of the present invention for therapeutic support of a wrist of a patient comprises a forearm support member and a hand engageable member. The forearm support member has a base portion engageable with a forearm of the patient and first and second side portions extending from the base portion and adapted for traversing opposite sides of the wrist of the patient when the forearm is engaged by the forearm support member. The hand engageable member has a hand grip adapted to support the palm or fingers of the patient and a hand grip support for spacing the hand grip from the forearm support member. The hand grip support comprises first and second side portions. The first side portion has a first grip securing region connected to a first end of the hand grip and a first wrist region. The second side portion has a second grip securing region connected to a second end of the hand grip and a second wrist region. At least one connector pivotally connects the first and second wrist regions to the first and second side portions of the forearm support member, respectively, for pivotal movement of the hand engageable member relative to the forearm support member from a wrist dorsiflexion position to a wrist palmarflexion position about a pivot axis generally coaxial with a wrist axis passing through the radioulnar joint of the wrist of the patient when the patient is wearing the wrist brace. The hand engageable member is lockable to the forearm support member by locking means in any one of a plurality of predetermined positions between the dorsiflexion position and the palmarflexion position.

Other advantages and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
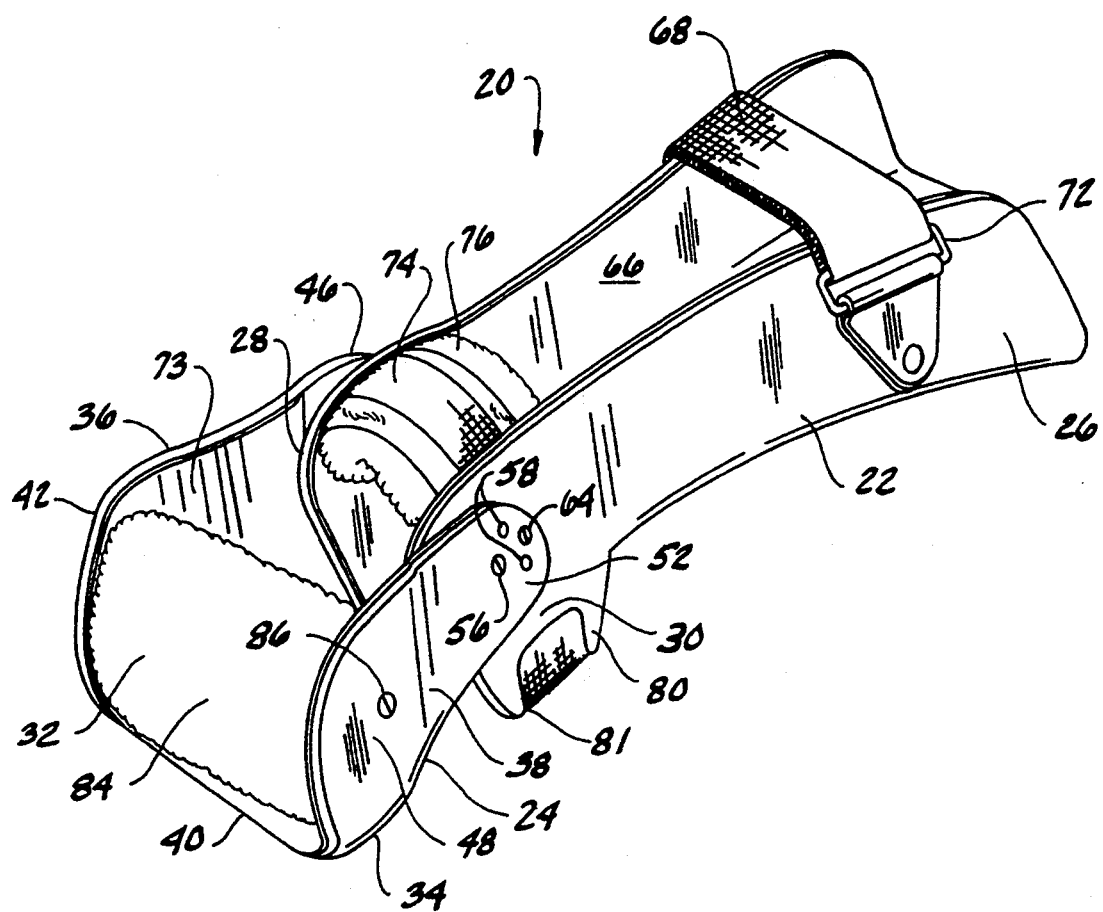
FIG. 1 is a perspective view of a wrist brace of the present invention having a forearm support member and a hand engageable member.

Referring to FIGS. 1-6, a wrist brace of this invention, generally indicated at 20, is shown to include a forearm support member 22 and a hand engageable member 24. The forearm support member 22 has a base portion 26 generally in the shape of an open channel or trough for receiving a forearm (shown in phantom in FIGS. 2-6) of a patient. First and second side portions 28 and 30 extend generally longitudinally forward from the base portion 26 and traverse opposite sides of the wrist (shown in phantom in FIGS. 2 and 3) of the patient when the forearm is placed in the base portion 26. The hand engageable member 24 has a hand grip 32 for supporting the palm or fingers of the patient and a hand grip support 34 for spacing the hand grip 32 from the forearm support member 22. The hand grip support 34 comprises first and second side portions 36 and 38 and a brace portion 40 spanning the side portions. The first side portion 36 has a first grip securing region 42 connected to a first end 44 of the hand grip 32 and a first wrist region 46 overlapping the first side portion 28. The second side portion 38 has a second grip securing region 48 connected to a second end 50 of hand grip 32 and a second wrist region 52 overlapping the second side portion 38. The brace portion 40 is spaced sufficiently from the hand grip 32 such that the brace portion 40 is spaced from the hand of the patient when the patient grasps the hand grip 32.

A first connector 54, such as a pin, screw or bolt/nut, pivotably connects the first wrist region 46 to the first side portion 28 of the forearm support member 22. A second connector 56, preferably identical to the first connector 54, pivotably connects the second wrist region 52 to the second side portion 30 of forearm support member 22. The connectors 54 and 56 allow pivotal movement of the hand engageable member 24 relative to the forearm support member 22 about a pivot axis $X_p$ (see FIGS. 2 and 3) passing through both connectors 54 and 56. The hand engageable member 24 is pivotable about the pivot axis $X_p$ and relative to the forearm support member 22 from a wrist dorsiflexion position (shown in FIG. 4) to a wrist palmarflexion position (shown in FIG. 6). The pivot axis $X_p$ is generally coaxial with a wrist axis passing through the radioulnar joint of the wrist of the patient when the patient is wearing the wrist brace 20. With the pivot axis $X_p$ coaxial to the wrist axis, the position (location) of the forearm support member 22 relative to the forearm of the patient and the position (location) of the hand engageable member 24 relative to the hand of the patient remain generally constant regardless of the pivot position of the wrist brace 20. Maintaining the forearm support member 22 in a constant position on the patient's forearm minimizes the discomfort to the patient when the pivot position is changed.

Figure 9:
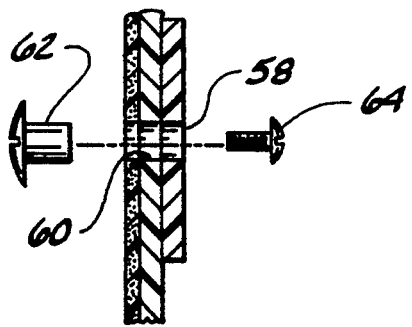
FIG. 9 is a cross-sectional view taken along the line 9—9 of FIG. 5.

The wrist regions 46 and 52 each have three through holes 58 each spaced approximately the same distance from the pivot axis $X_p$. Each side portion 28 and 30 of forearm support member 22 has a single through hole 60 (see FIGS. 6 and 9) spaced the same distance from the pivot axis $X_p$ as that of holes 58. The hole 60 through each side portion 28 and 30 is alignable with each of the three holes 58 through the corresponding wrist regions 46 and 52 upon pivotal movement of the hand engageable member 24 relative to the forearm support member 22. A pin-type fastener 62 (see FIG. 9) extends through hole 60 and one of the three holes 58 and mates with a screw 64 for releasably securing the hand engageable member 24 to the forearm support member 22 in fixed relation thereto. The holes 58 and 60 constitute locking sites at which the hand engageable member 24 may be locked to the forearm support member 22. The locking sites and fasteners 62 constitute means for locking the hand engageable member 24 to the forearm support member 22 in any one of a plurality of predetermined pivot positions between the dorsiflexion position and the palmarflexion position. The combinations of alignment of the locking sites on the forearm support 22 (i.e., hole 60) with the locking sites on the hand engageable member 24 correspond to the plurality of predetermined pivot positions. The preferred embodiment has three predetermined positions, shown in FIGS. 4–6. The number of predetermined pivot positions may be increased by increasing the number of alignment holes 58 in the hand engageable member 24 and/or by increasing the number of alignment holes 60 in the forearm support member 22.

In an alternative construction, an arcuate slot may replace the holes in the hand engageable member and a bolt/wing-nut assembly may extend through the slot and through a hole in the forearm support member. The pivot position of the hand engageable member relative to the forearm support member may be varied by loosening the wing-nut, pivoting the hand engageable member, and then tightening the wing-nut. The hand engageable member may also include measuring indicia adjacent the slot to set a precise pivot position.

Figure 2:
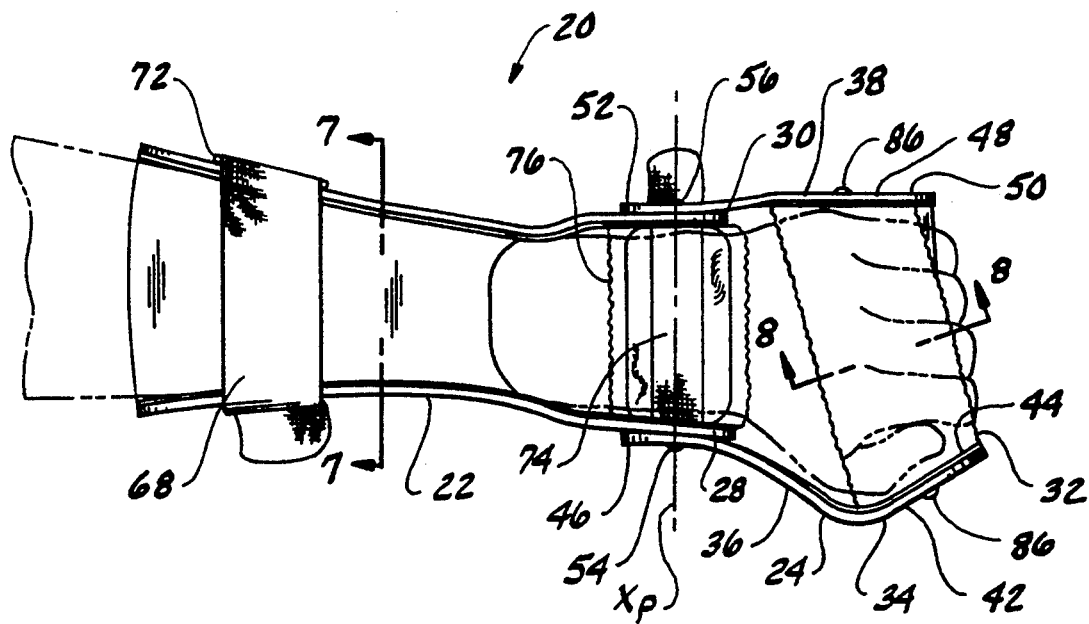
FIG. 2 is a top plan view of the wrist brace of FIG. 1 being worn on the arm and hand (shown in phantom) of a patient.
Figure 3:
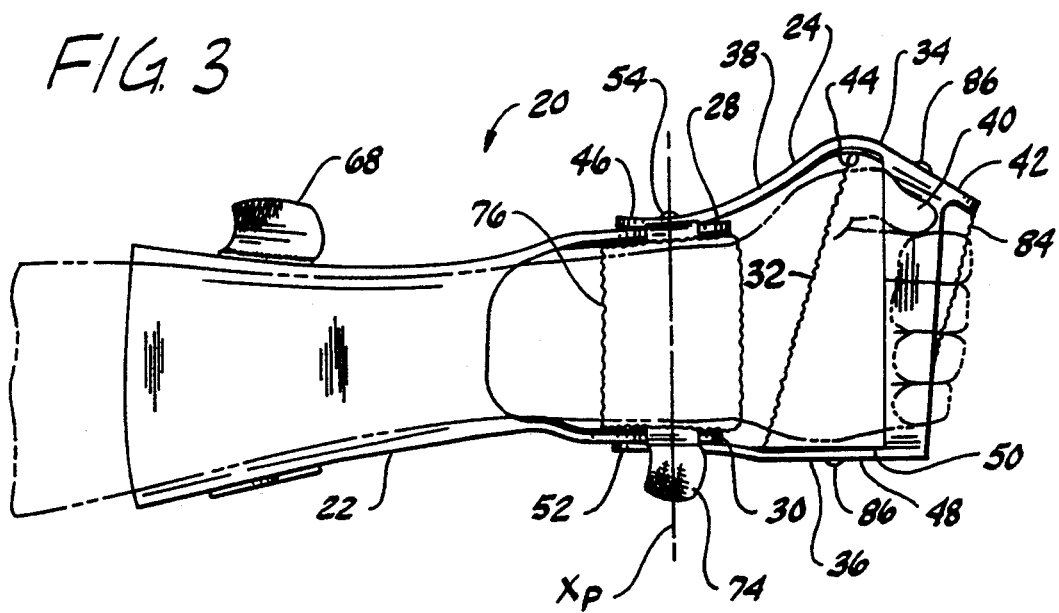
FIG. 3 is a bottom plan view of the wrist brace of FIG. 1 being worn on the arm and hand (shown in phantom) of a patient.
Figure 4:
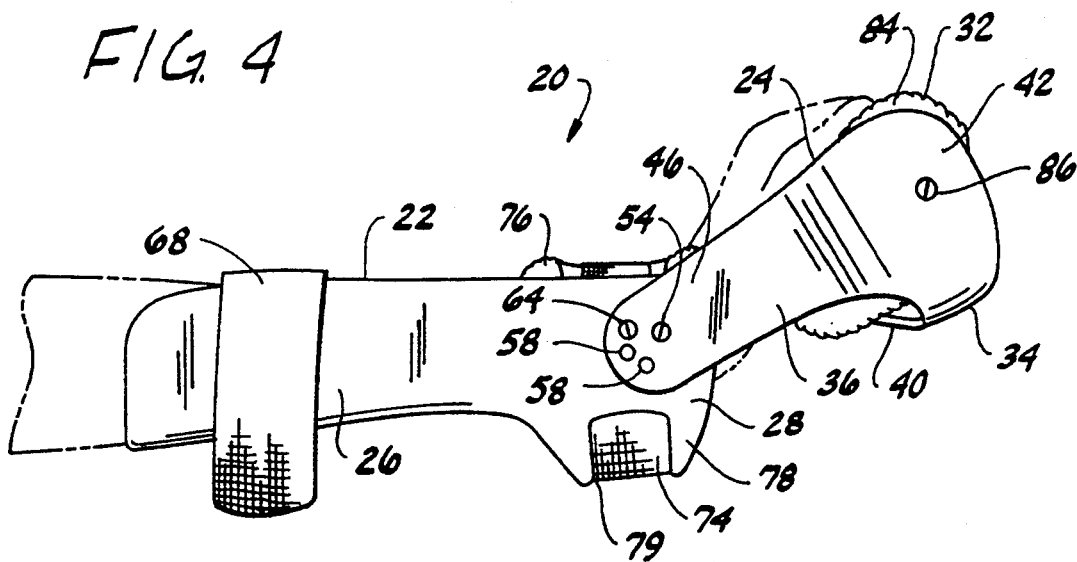
FIG. 4 is a side elevational view of the wrist brace of FIG. 1 in a dorsiflexion position.
Figure 5:
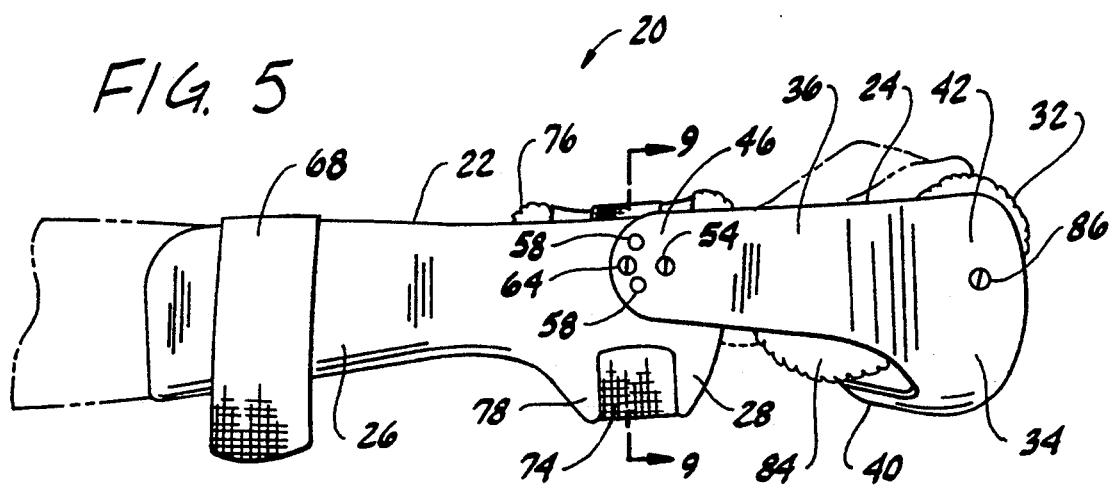
FIG. 5 is a side elevational view of the wrist brace of FIG. 1 in a neutral position.
Figure 6:
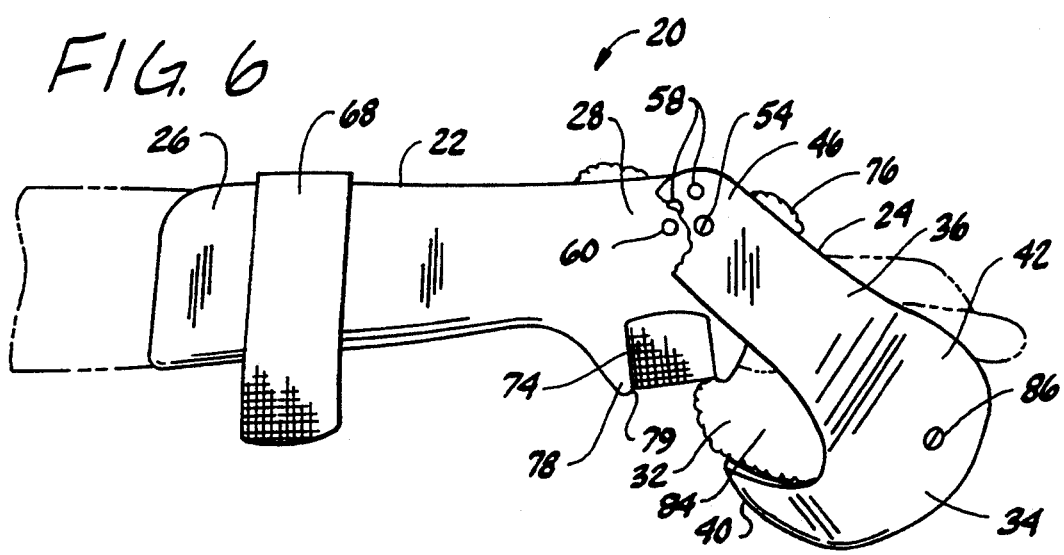
FIG. 6 is a side elevational view of the wrist brace of FIG. 1 in a palmarflexion position with a portion of the hand engageable member broken away to show detail.
Figure 7:
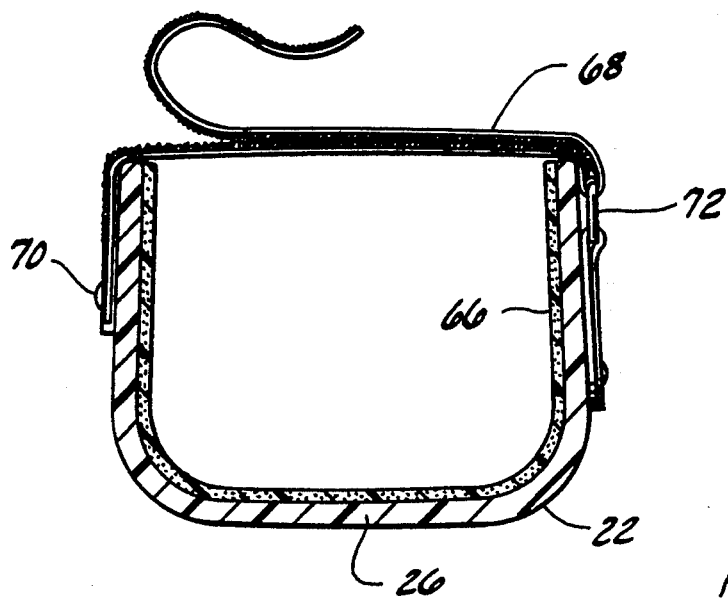
FIG. 7 is a cross-sectional view taken along the line 7—7 of FIG. 2.

As shown in FIGS. 2, 3 and 7, the base portion 26 of the forearm support member 22 is configured to substantially surround the forearm of the patient and has a generally U-shaped cross-section (see FIG. 7) which defines an open top to facilitate insertion of the patient's forearm therein. Preferably, the forearm support member 22 is an integral one-piece member formed of a molded polymeric resin, such as polypropylene. Also, the forearm support member 22 preferably includes a forearm pad 66 of a yieldable material (such as a closed-cell foam manufactured by Alimed Inc., under the trademark Aliplast) bonded to the inside surface of support member 22 to minimize discomfort to the patient. A forearm strap 68 is fixedly secured adjacent one of its ends to one side of the base portion 26 by a fastener 70 and is looped through a ring 72 fastened to the opposite side of the base portion. Preferably, the strap 68 has hook and loop type fastening strips secured thereto for adjustably securing the base portion 26 on the forearm of the patient.

As shown in FIGS. 1–3, a wrist strap 74 is releasably secured to the side portions 28 and 30 of the forearm support member 22. Hook-type fastening strips (not shown) are secured to opposite end margins of the wrist strap 74 and are mateable with loop-type fastening strips (not shown) secured to the outwardly facing surfaces of the side portions 28 and 30. A wrist pad 76, preferably made of lamb's wool, is sewn or bonded to an intermediate portion of the wrist strap 74 and is adapted to contact the dorsum portion of the wrist. One end margin of the strap 74 is releasably secured to a lower portion 78 of the first side portion 28, the lower portion 78 extending downwardly below the base 26. The intermediate portion of the strap closely traverses the inside surface of the first side portion 28 and traverses the dorsum of the patient's wrist (with the wrist pad 76 pressed against the dorsum of the wrist by the central portion of the strap) and closely traverses the inside surface of the second side portion 30, and the other end margin of the strap 74 is releasably secured to a lower portion 80 of the second side portion 30, the lower portion 80 extending downward below the base 26. The lower portions 78 and 80 include recesses 79 and 81, respectively, to resist lateral movement of the strap 74.

Figure 8:
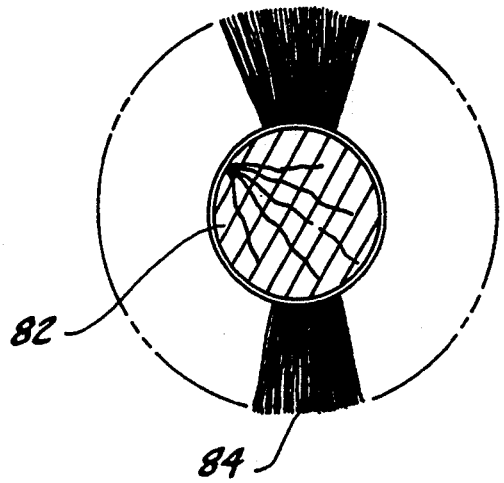
FIG. 8 is a cross-sectional view taken along the line 8—8 of FIG. 2.

The hand grip support 34 is preferably an integral one-piece member formed of a molded polymeric resin, such as polypropylene. The inside surface of the hand grip support 34 is lined with a yieldable pad 73 of the same material as that of pad 66. As shown in FIG. 8, the hand grip 32 preferably has a solid wooden core 82 surrounded by a hand pad 84, preferably made of lamb's wool. The hand grip 32 is connected to the hand grip support 34 by two wood screws 86 passing through holes (not shown) in side portions 36 and 38 of grip support 34 and threaded into opposite ends of the core 82 of hand grip 32. Alternatively, the hand grip may be secured to the hand grip support by a bolt passing through both side portions of the hand grip support and through a central bore in the core of the hand grip.

In operation, the hand engageable member 24 is pivoted relative to the forearm support member 22 to a desired pivot position in which each hole 60 aligns with a corresponding one of the holes 58. Fastener 62 are then inserted through each pair of aligned holes to fix the wrist brace 20 at the desired pivot position. The patient's hand grasps the hand grip 32 and the patient's forearm is inserted into the base portion 26 of the forearm support member 22. The forearm strap 68 is tautly secured over the patient's forearm and the wrist strap 74 is tautly secured over the patient's wrist to press the wrist pad 76 against the dorsum portion of the wrist. The hand grip 32, wrist strap 74, and forearm support member 22 cooperate to act as a fulcrum to urge the patient's wrist to the desired pivot position. To change the pivot position, the wrist brace 20 is removed from the patient's hand and forearm, the fasteners 62 are removed, and the hand engageable member 24 is pivoted to the new desired pivot position. The fasteners 62 are then reinserted to lock the wrist brace 20 in its new desired pivot position and the wrist brace 20 is placed back onto the patient's forearm and hand. Because the pivot axis $X_p$ of the wrist brace 20 is coaxial with the wrist axis of the patient, the orientation of the base portion 26 relative to the patient's forearm remains substantially unchanged from pivot position to pivot position.

In view of the above, it will be seen that the several objects of the invention are achieved and other disadvantageous results attained.

As various changes could be made in the above construction without departing from the scope of the invention, it is intended that all matter contained in the above description or shown in the accompanying drawings shall be interpreted as illustrative and not in a limiting sense.

What is claimed is:

1. A wrist brace for therapeutic support of a wrist of a patient comprising:
   a forearm support member having a base portion engageable with a forearm of the patient and first and second side portions extending from the base portion and adapted for traversing opposite sides of the wrist of the patient when the forearm is engaged by the forearm support member;
   a hand engageable member having a hand grip adapted to support the palm or fingers of the patient and a hand grip support for spacing the hand grip from the forearm support member, said hand grip support comprising a first side portion having a first grip securing region connected to a first end of the hand grip and having a first wrist region, and a second side portion having a second grip securing region connected to a second end of the hand grip and having a second wrist region;
   a forearm strap for releasably securing the base portion of the forearm support member to the forearm of the patient;
   a wrist strap secured adjacent the side portions of the forearm support member for engaging the dorsum of the wrist of the patient;
   at least one connector pivotally connecting said first and second wrist regions to the first and second side portions of the forearm support member, respectively, for pivotal movement of the hand engageable member relative to the forearm support member from a wrist dorsiflexion position to a wrist palmarflexion position about a pivot axis generally coaxial with a wrist axis passing through the radioulnar joint of the wrist of the patient when the patient is wearing the wrist brace; and
   means for locking the hand engageable member to the forearm support member in any one of a plurality of predetermined positions between the dorsiflexion position and the palmarflexion position to prevent relative movement between the hand engageable member and the forearm support member.

2. A wrist brace as set forth in claim 1 wherein said locking means comprises a plurality of locking sites formed on one of said hand engageable member and forearm support member, at least one locking site formed on the other of said hand engageable member and forearm support member alignable with each of said plurality of locking sites upon movement of the hand engageable member relative to the forearm support member, and a fastener for releasably securing said at least one locking site to any one of said plurality of locking sites, the combinations of said at least one locking site with said plurality of locking sites corresponding to said plurality of predetermined positions.

3. A wrist brace as set forth in claim 2 wherein one of said hand engageable member and forearm support member includes a plurality of holes constituting said plurality of locking sites and wherein the other of said hand engageable member and forearm support member includes at least one hole constituting said at least one locking site and wherein said fastener comprises a pin positionable in one of the plurality of holes and in said at least one hole.

4. A wrist brace as set forth in claim 1 wherein said hand grip support further comprises a brace portion spanning the side portions thereof, said brace portion being spaced sufficiently from the hand grip such that the brace portion is spaced from the hand of the patient when the patient grasps the hand grip with such hand.

5. A wrist brace as set forth in claim 4 wherein said hand grip support comprises an integral one piece member formed of molded polymeric resin.

6. A wrist brace as set forth in claim 5 wherein said base portion of said forearm support member has a generally U-shaped cross-section and substantially surrounds the forearm.

7. A wrist brace as set forth in claim 6 wherein said forearm support member comprises an integral one piece member formed of molded polymeric resin.

8. A wrist brace for therapeutic support of the wrist of a patient comprising:
   a forearm support member having a base portion engageable with a forearm of the patient and first and second side portions extending from the base portion and adapted for traversing opposite sides of the wrist of the patient when the forearm is engaged by the forearm support member;
   a hand engageable member having a hand grip adapted to support the palm or fingers of the patient and a hand grip support for spacing the hand grip from the forearm support member, said hand grip support comprising a first side portion having a first grip securing region connected to a first end of the hand grip and having a first wrist region, a second side portion having a second grip securing region connected to a second end of the hand grip and having a second wrist region, and a brace portion spanning the first and second side portions of the hand grip spaced sufficiently from the hand grip such that the brace is spaced from the hand of the patient when the patient grips the hand grip with such hand;
   a forearm strap for releasably securing the base portion of the forearm support member to the forearm of the patient;
   a wrist strap secured adjacent the side portions of the forearm support member for engaging the dorsum of the wrist of the patient;
   said hand engageable member and said forearm support member each comprising an integral one piece member formed of molded polymeric resin;
   at least one connector pivotally connecting said first and second wrist regions to the first and second side portions of the forearm support member, respectively, for pivotal movement of the hand engageable member relative to the forearm support member from a wrist dorsiflexion position to a wrist palmarflexion position; and means for locking the hand engageable member to the forearm support member in any one of a plurality of predetermined positions between the dorsiflexion position and the palmarflexion position to prevent relative movement between the hand engageable member and the forearm support member.

9. A wrist brace as set forth in claim 8 wherein said base portion of said forearm support member has a generally U-shaped cross-section and substantially surrounds the forearm.

10. A wrist brace as set forth in claim 8 wherein said locking means comprises a plurality of locking sites formed on one of said hand engageable member and forearm support member, at least one locking site formed on the other of said hand engageable member and forearm support member alignable with each of said plurality of locking sites upon movement of the hand engageable member relative to the forearm support member, and a fastener for releasably securing said at least one locking site to any one of said plurality of locking sites, the combinations of said at least one locking site with said plurality of locking sites corresponding to said plurality of predetermined positions.

11. A wrist brace as set forth in claim 10 wherein one of said hand engageable member and forearm support member includes a plurality of holes constituting said plurality of locking sites and wherein the other of said hand engageable member and forearm support member includes at least one hole constituting said at least one locking site and wherein said fastener comprises a pin positionable in one of the plurality of holes and in said at least one hole.

12. A wrist brace as set forth in claim 8 wherein said hand grip support further comprises a brace portion spanning the side portions thereof, said brace portion being spaced sufficiently from the hand grip such that the brace portion is spaced from the hand of the patient when the patient grasps the hand grip with such hand.

* * * * *